United States Patent
Cai et al.

(10) Patent No.: US 11,707,243 B2
(45) Date of Patent: Jul. 25, 2023

(54) SCATTER AND RANDOM COINCIDENCE REJECTION

(71) Applicant: CANON MEDICAL SYSTEMS CORPORATION, Otawara (JP)

(72) Inventors: Liang Cai, Vernon Hills, IL (US);
Wenyuan Qi, Vernon Hills, IL (US);
Xiaochun Lai, Vernon Hills, IL (US);
Peng Peng, Vernon Hills, IL (US)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 63 days.

(21) Appl. No.: 17/230,499

(22) Filed: Apr. 14, 2021

(65) Prior Publication Data

US 2022/0330907 A1    Oct. 20, 2022

(51) Int. Cl.
| A61B 6/00 | (2006.01) |
| G01T 1/24 | (2006.01) |
| G01T 1/172 | (2006.01) |
| A61B 6/03 | (2006.01) |

(52) U.S. Cl.
CPC ............ *A61B 6/5205* (2013.01); *A61B 6/037* (2013.01); *G01T 1/172* (2013.01); *G01T 1/248* (2013.01); *G01T 1/249* (2013.01)

(58) Field of Classification Search
CPC ....... A61B 6/037; A61B 6/5205; G01T 1/172; G01T 1/248; G01T 1/249
See application file for complete search history.

(56) References Cited

U.S. PATENT DOCUMENTS

| 5,821,541 | A  | * | 10/1998 | Turner | G01T 1/2928 |
| | | | | | 250/363.03 |
| 6,346,706 | B1 | * | 2/2002 | Rogers | A61B 6/037 |
| | | | | | 250/363.04 |
| 6,791,090 | B2 | * | 9/2004 | Lin | G01T 1/242 |
| | | | | | 250/336.1 |
| 2002/0011571 | A1 | * | 1/2002 | Lin | G01T 1/242 |
| | | | | | 250/366 |
| 2006/0138332 | A1 | | 6/2006 | Bryman | |
| 2006/0202125 | A1 | * | 9/2006 | Suhami | G01T 1/202 |
| | | | | | 250/368 |

(Continued)

OTHER PUBLICATIONS

Doost-Mohammadi ; Simulation of beta-gamma coincidence spectra of radioxenon detector using gate 7.0 and comparison with experimental results ; Journal of Radioanalytical and Nuclear Chemistry ; Feb. 2016 ; 9 Pages.

(Continued)

*Primary Examiner* — Blake C Riddick
(74) *Attorney, Agent, or Firm* — Oblon, McClelland, Maier & Neustadt, L.L.P.

(57) ABSTRACT

Multiple interactions, such as Compton scattering, inside a PET detector are used to predict an incident photon's direction for identifying true coincidence events versus scatter/random coincidence events by creating a cone shaped shell projection defining a range of possible flight directions for the incident photon. The disclosed techniques can be used as prior information to improve the image reconstruction process. The disclosed techniques can be implemented in a LYSO/SiPM-based layer stacked detector, which can precisely register multiple interactions' 3D position.

20 Claims, 6 Drawing Sheets

(56) References Cited

U.S. PATENT DOCUMENTS

| | | | |
|---|---|---|---|
| 2007/0152162 A1* | 7/2007 | Griesmer | G01T 1/2985 |
| | | | 250/363.09 |
| 2010/0148075 A1* | 6/2010 | Chinn | A61B 6/037 |
| | | | 250/363.04 |
| 2012/0114100 A1 | 5/2012 | Gueorguiev et al. | |
| 2014/0072200 A1* | 3/2014 | Yamaguchi | G06T 7/0012 |
| | | | 382/132 |
| 2015/0331115 A1* | 11/2015 | Nelson | G01T 1/1611 |
| | | | 250/366 |
| 2018/0239037 A1 | 8/2018 | Yamaya et al. | |
| 2018/0252825 A1* | 9/2018 | Benlloch Baviera | |
| | | | G01T 1/2002 |
| 2019/0094390 A1* | 3/2019 | Polf | G01T 1/167 |
| 2019/0353808 A1* | 11/2019 | Watanabe | G01T 1/2985 |
| 2021/0007682 A1* | 1/2021 | Chmeissani Raad | |
| | | | A61B 6/5205 |
| 2021/0282725 A1* | 9/2021 | Rodrigues | G01T 1/29 |

OTHER PUBLICATIONS

Peng, et al. ;Compton PET: a layered structure PET detector withhigh performance ; Physics in Medicine and Biolofy, vol. 64, No. 10 ; May 8, 2019 ; 3 Pages.

\* cited by examiner

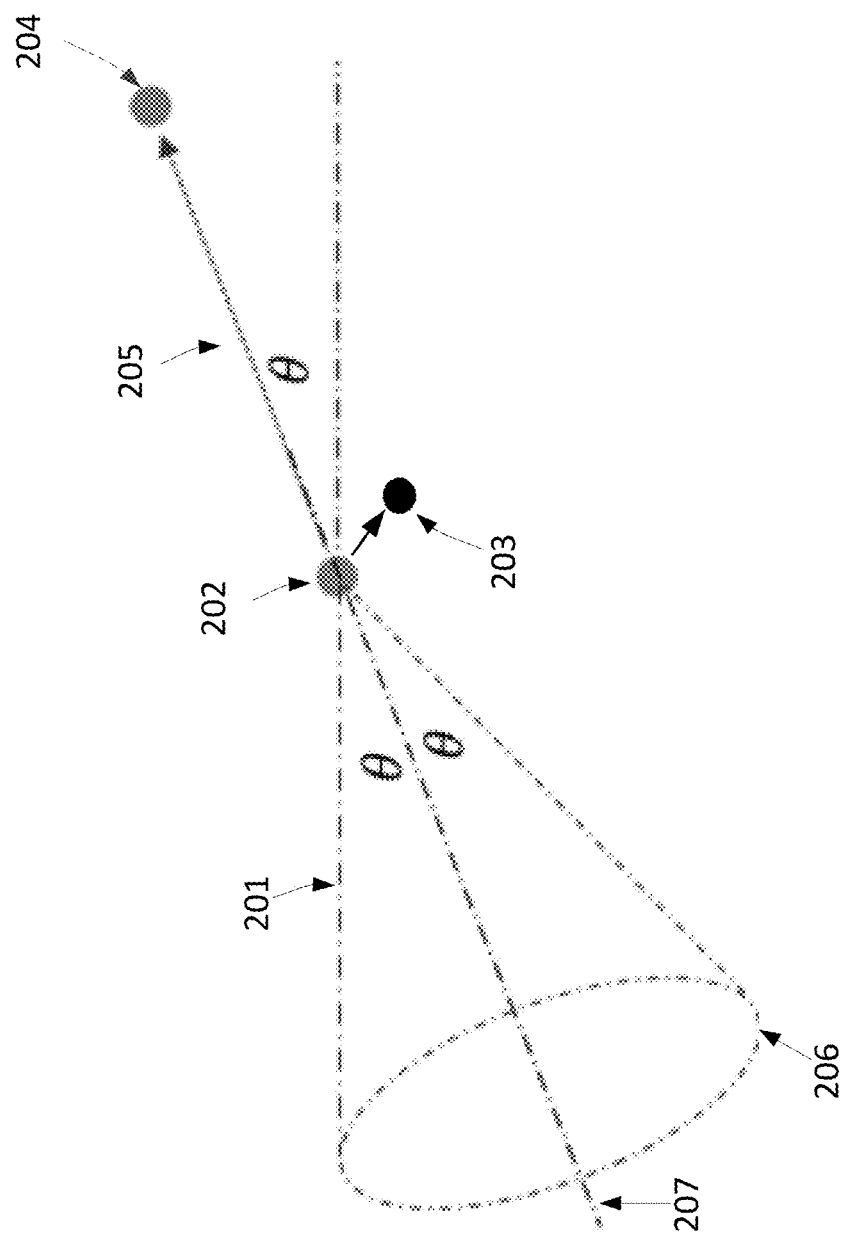

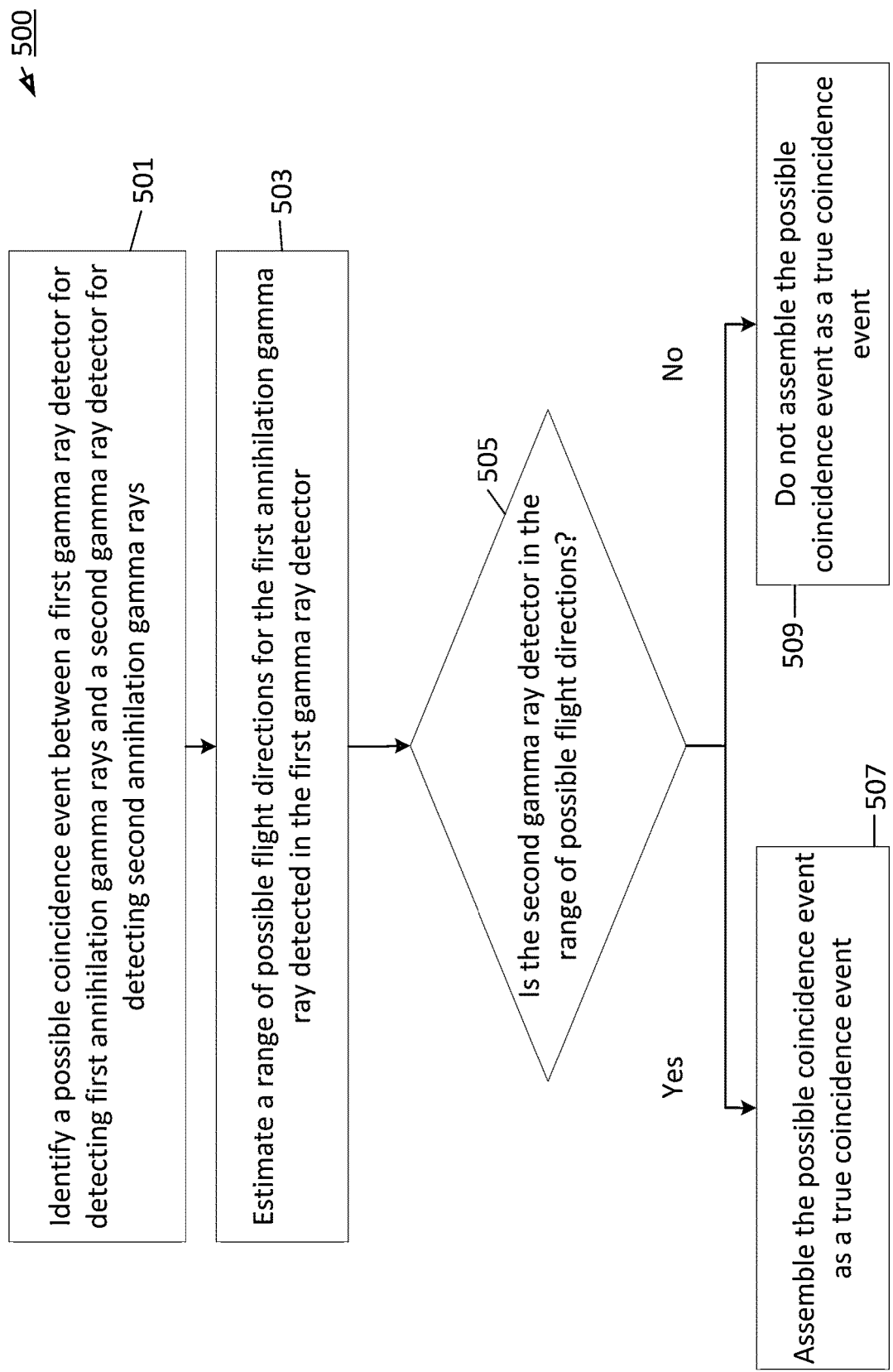

SCATTER AND RANDOM COINCIDENCE REJECTION

FIELD OF THE INVENTION

Embodiments described herein relate generally to a system and method for scattered and random coincidence event rejection in a nuclear medical diagnostic apparatus.

BACKGROUND

In PET systems, positron annihilation generated back-to-back gamma ray pairs are detected by surrounding detectors. The detection pairs are typically captured and assembled by setting up coincidence windows in PET detectors. In practical cases, the true detection pairs are often contaminated by scatter events and random events. These scatter and random events contaminate true PET coincidence events, which degrade image quality.

One technique to remove scattered events in PET data acquisition is to cut the energy window, as scattered events have less energy due to scatter effects. However, there is still a large amount of scattered events that fall within the allowable energy window.

In light of the above mentioned problems, there exists a need to better differentiate between true coincidence events and scatter/random coincidence events.

SUMMARY

Disclosed is a nuclear medical diagnostic apparatus comprising: first and second gamma ray detectors for detecting first and second annihilation gamma rays, respectively; processing circuitry configured to, identify a possible coincidence event between the first gamma ray detector and the second gamma ray detector; and estimate a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector.

In one exemplary embodiment, the processing circuitry is further configured to assemble the possible coincidence event as a true coincidence event if the second gamma ray detector corresponds to the range of possible flight directions and to not assemble the possible coincidence event as a true coincidence event if the second gamma ray detector does not correspond to the range of possible flight directions.

In one exemplary embodiment, the processing circuitry configured to estimate the range of possible flight directions comprises processing circuitry configured to estimate the range of possible flight directions for the first annihilation gamma ray detected in the first gamma ray detector based on a location of the Compton scatter event (e.g. recoiled electron) in the first gamma ray detector, an energy of the Compton scatter event in the first gamma ray detector, a location of a second event (e.g. scattered photon), and an energy of the second event, wherein the second event is caused by the Compton scatter event.

In one exemplary embodiment, the range of possible flight directions comprises flight directions based on a variability of the energy of the Compton scatter event and the energy of the second event, the variability being caused by a limited energy resolution of the nuclear medical diagnostic apparatus.

In one exemplary embodiment, the range of possible flight directions comprises flight directions based on a variability of the location of the Compton scatter event and the location of the second event, the variability being caused by a limited spatial resolution of the nuclear medical diagnostic apparatus.

In one exemplary embodiment, the range of possible flight directions corresponds to a cone shaped shell projection, the cone shaped shell projection having an apex point at the location of the Compton scatter event (e.g. recoil electron), an axis in line with the location of the Compton scatter event and the location of the second event (e.g. scattered photon), and a half angle based on the energy of the Compton scatter event and the energy of the second event.

In one exemplary embodiment, the nuclear medical diagnostic apparatus is a layer stacked PET detector.

In one exemplary embodiment, the first gamma ray detector and the second gamma ray detector comprise lutetium yttrium oxyorthosilicate.

In one exemplary embodiment, the first gamma ray detector and the second gamma ray detector comprise one or more silicon photomultipliers.

Also disclosed is a method for collecting coincidence data in a nuclear medical diagnostic apparatus having a first and second gamma ray detector for detecting first and second annihilation gamma rays, respectively, comprising: identifying a possible coincidence event between the first gamma ray detector and the second gamma ray detector; and estimating a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector.

In one exemplary embodiment, the method further comprises assembling the possible coincidence event as a true coincidence event if the second gamma ray detector corresponds to the range of possible flight directions and to not assemble the possible coincidence event as a true coincidence event if the second gamma ray detector does not correspond to the range of possible flight directions.

In one exemplary embodiment, the estimating the range of possible flight directions comprises estimating the range of possible flight directions for the first annihilation gamma ray detected in the first gamma ray detector based on a location of the Compton scatter event in the first gamma ray detector, an energy of the Compton scatter event in the first gamma ray detector, a location of a second event, and an energy of the second event, wherein the second event is caused by the Compton scatter event.

In one exemplary embodiment, the range of possible flight directions comprises flight directions based on a variability of the energy of the Compton scatter event and the energy of the second event, the variability being caused by a limited energy resolution of the nuclear medical diagnostic apparatus.

In one exemplary embodiment, the range of possible flight directions comprises flight directions based on a variability of the location of the Compton scatter event and the location of the second event, the variability being caused by a limited spatial resolution of the nuclear medical diagnostic apparatus.

In one exemplary embodiment, the range of possible flight directions corresponds to a cone shaped shell projection, the cone shaped shell projection having an apex point at the location of the Compton scatter event, an axis in line with the location of the Compton scatter event and the location of the second event, and a half angle based on the energy of the Compton scatter event and the energy of the second event.

In one exemplary embodiment, the nuclear medical diagnostic apparatus is a layer stacked PET detector.

In one exemplary embodiment, the first gamma ray detector and the second gamma ray detector comprise lutetium yttrium oxyorthosilicate.

In one exemplary embodiment, the first gamma ray detector and the second gamma ray detector comprise one or more silicon photomultipliers.

Also disclosed is a non-transitory computer-readable medium including computer-readable instructions that, when executed by a computing system, cause the computing system to sort data by performing a method comprising: identifying a possible coincidence event between a first gamma ray detector for detecting a first annihilation gamma ray and a second gamma ray detector for detecting a second annihilation gamma ray; and estimating a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF DRAWINGS

FIG. 2B illustrates an example of utilizing Compton scatter to estimate a range of possible flight directions.

FIG. 5 is a flowchart of a method for collecting coincidence data according to one exemplary aspect of the present disclosure.

DETAILED DESCRIPTION

Figure 1:
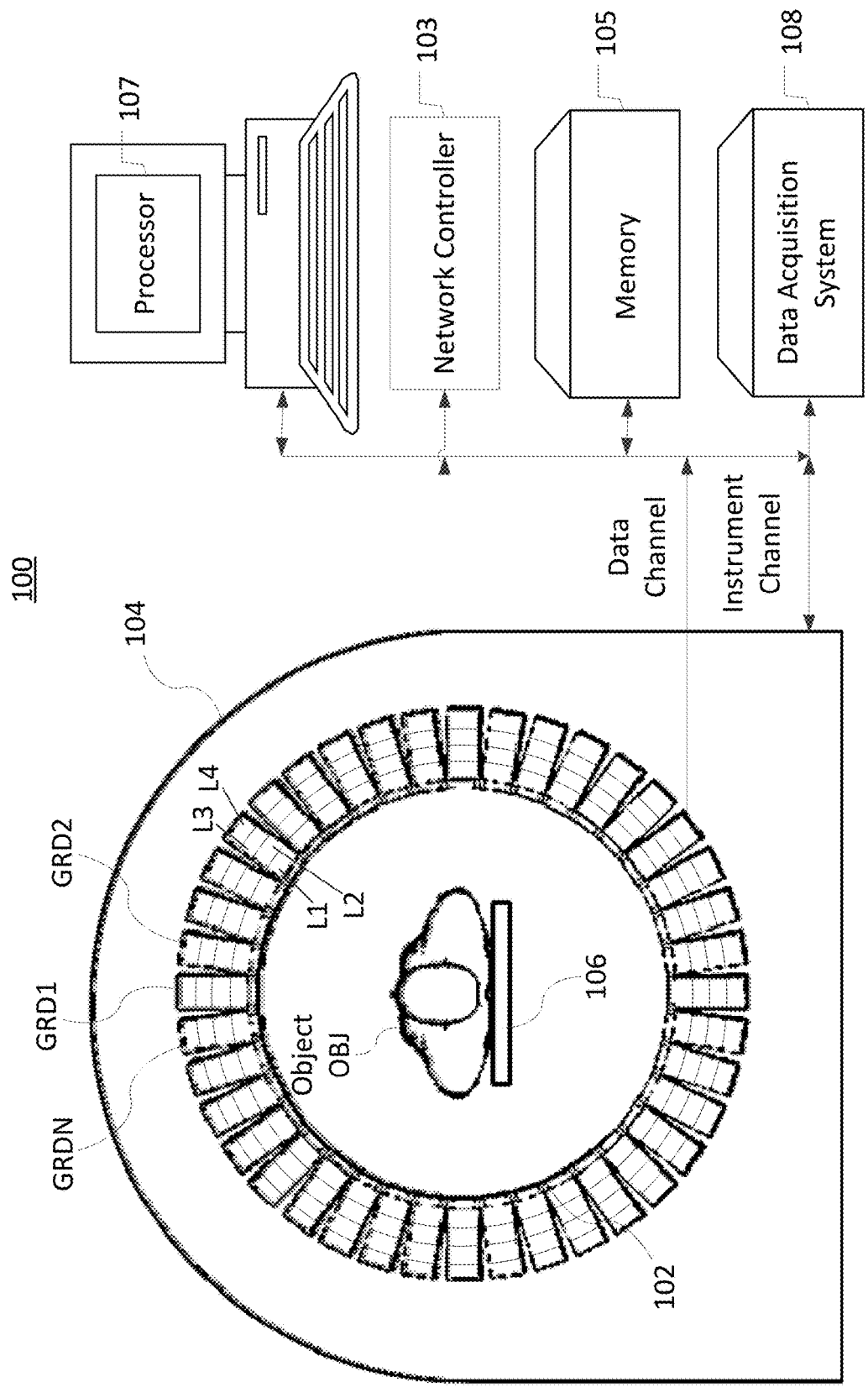
FIG. 1 shows an example of a layer stacked PET scanner system.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways. This disclosure describes a layer stacked PET detector to illustrate the various embodiments, but these concepts can be applied to similar systems. Further, as used herein, the words "a", "an" and the like generally carry a meaning of "one or more", unless stated otherwise.

A difficulty in determining whether an event pair is a true or scatter/random coincidence is that there is no information on the incident gamma ray's direction. If such information can be derived, it's possible to sort out the true coincidence event pairs. Gamma rays hit and interact with PET detectors under several different physics principles, such as Compton scatter. If multiple interactions inside the PET detector can be captured, the recorded energy and location information can be used to derive the incident photon's direction(s). Following this principle, for each recorded events series under Compton scattering, a range of possible flight directions in which the incident gamma ray may have come from can be estimated. Techniques disclosed herein include utilizing multiple interactions inside a PET detector to predict the incident photon's direction. Such prediction can be used to efficiently reject scattered coincidence events and random coincidence events in PET systems.

In one embodiment, it can be appreciated that the present disclosure may be implemented within a layer stacked PET scanner, which can precisely register multiple interactions' energy and 3D positions for predicting the incident photon's direction. See, for example, (1) Peng Peng et al 2019 Biomed. Phys. Eng. Express 5 015018, and (2) Peng Peng et al 2019 Phys. Med. Biol. 64 10LT01, the disclosures of these references being incorporated herein their entirety by reference. FIG. 1 show one embodiment of a layer stacked PET scanner 100 including a number of gamma-ray detectors (GRDs) (e.g., GRD1, GRD2, through GRDN) that are each configured as detector modules. Each GRD is layered using crystal slabs (L1, L2, L3, and L4) stacked in the depth direction so that energy deposited by the gamma rays in each layer can be measured separately. Using such a layered structure can allow for the PET scanner 100 to more precisely detect Compton scattering events.

According to one implementation, each PET detector ring, which forms a circular bore 102 about a gantry 104, includes a number of GRDs (e.g., 40 or 48). The translation of each PET detector ring may be accomplished by manual manipulation and/or motorized manipulation. The GRDs include scintillator crystal arrays at each crystal slab L1, L2, L3, L4 for converting the gamma rays into scintillation photons (e.g., at optical, infrared, and ultraviolet wavelengths), which are detected by photodetectors. Each crystal slab L1, L2, L3, L4 can be made of lutetium-yttrium oxyorthosilicate (LYSO) and be read out by a 4×4 silicon photomultiplier (SiPM) array (matching the crystal layer pitch) to measure scintillation light within each crystal slab L1, L2, L3, L4. Enhanced specular reflector (ESR) film can be glued between each crystal slab L1, L2, L3, L4 so that energy deposited by the gamma rays in each layer of the crystal slab L1, L2, L3, L4 can be measured separately. Optical grease (e.g. BC-630) can be used between the crystal slabs L1, L2, L3, L4 and the SiPMs. Analog signals from all the SiPMs (4×16) on the four sides of the crystal can be digitized individually using a 64-channel TOFPET-2 module.

FIG. 1 shows the layer stacked PET scanner 100 having GRDs arranged to detect gamma-rays emitted from an object OBJ (e.g., a patient). The GRDs can measure the timing, position, and energy corresponding to each gamma-ray detected. Because the GRDs use a layered structure, the measured position can include information on which layer of the GRD the energy was deposited in. In one implementation, the gamma-ray detectors are arranged in a PET detector ring. It can be appreciated that the single PET detector ring of FIG. 1 can be extrapolated to include any number of PET detector rings along an axial length of the PET scanner 100. The detector crystals in each crystal slab L1, L2, L3, L4 can be scintillator crystals, which have individual scintillator elements arranged in a two-dimensional array, and the scintillator elements can be any known scintillating material. The crystal slabs L1, L2, L3, L4 are not limited to being LYSO, and can be made of any known scintillating material. Each crystal slab L1, L2, L3, L4 can be made of different materials, and any number of crystal slabs can be used. The photomultipliers can be arranged such that light from each scintillator element is detected by multiple photomultipliers to enable Anger arithmetic and crystal decoding of scintillation event.

FIG. 1 shows an example of the arrangement of the layer stacked PET scanner 100, in which an object OBJ (e.g., a possibly infected person) rests on a table 106 and the GRD modules GRD1 through GRDN are arranged circumferentially around the object OBJ (e.g., a patient) and the table 106. The GRDs may comprise a PET detector ring and may fixedly-connected to a circular bore 102 that is fixedly-connected to a gantry 104. The gantry 104 houses many parts of the layer stacked PET scanner 100. The gantry 104 of the layer stacked PET scanner 100 also includes an open aperture, defined by the cylindrical bore 102, through which the object OBJ (e.g., a patient) and the table 106 can pass, and gamma-rays emitted in opposite directions from the object OBJ (e.g., a patient) due to an annihilation event can be detected by the GRDs and timing and energy information can be used to determine coincidences for gamma-ray pairs.

In FIG. 1, circuitry and hardware is also shown for acquiring, storing, processing, and distributing gamma-ray detection data. The circuitry and hardware include a processor 107, a network controller 103, a memory 105, and a data acquisition system (DAS) 108. The PET imager also includes a data channel that routes detection measurement results from the GRDs to the DAS 108, the processor 107, the memory 105, and the network controller 103. The data acquisition system 108 can control the acquisition, digitization, and routing of the detection data from the detectors. In one implementation, the DAS 108 controls the movement of the table 106. The processor 107 performs functions including pre-reconstruction processing of the detection data, image reconstruction, and post-reconstruction processing of the image data. According to one exemplary aspect, the processor 107 can perform method 500, which is discussed below.

Note that FIG. 1 illustrates one embodiment of a layer stacked PET detector, and other configurations can be implemented without deviating from the core concepts of this disclosure. Examples of configuration tweaks can include, but are not limited to: the crystal slabs L1, L2, L3, L4 can be made of materials other than LYSO; the photomultiplier array can be made of material other than silicon; each crystal slab L1, L2, L3, L4 can be made of the same material or multiple different materials; more or less than four crystal slab layers can be used in each GRD; the photomultiplier array can be any dimension, etc.

Figure 2A:
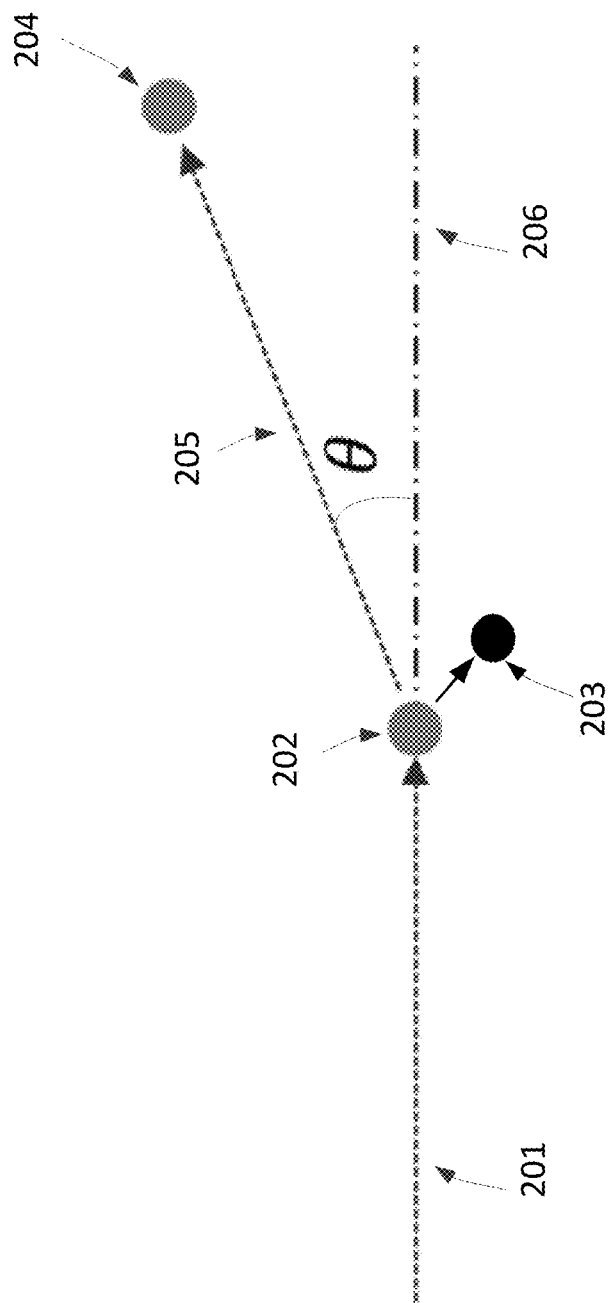
FIG. 2A illustrates an example of Compton scatter.

Compton scattering can occur within and between crystal slabs L1, L2, L3, L4 (of the same GRD or adjacent GRDs). This Compton scattering can be detected by the components of the PET scanner 100 and used to predict a range of possible flight directions for the incident gamma ray. During Compton scattering, an incident gamma ray (i.e. incident photon) hits an electron, which causes the incident photon to scatter at a different wavelength, and the electron to recoil. The concept is illustrated using FIG. 2A, which shows the flight direction for the incident photon 201, the location 202 of the Compton scatter event where the incident photon first hit the electron, the recoiled electron 203, the flight direction of the scattered photon 205, and the location 204 where the scattered photon deposited. The layer stacked PET scanner 100 can measure/determine the flight direction of the scattered photon 205 (i.e. straight line connecting location 202 and location 204), the recoiled electron 203 energy, and the deposited energy of the scattered photon at location 204 to generate a range of possible flight directions for the incident photon using equation (1) and equation (2) below:

$$E' = \frac{E}{1 + \frac{E}{m_e c^2}(1 - \cos\theta)} \quad (1)$$

$$E_e = E\left[1 - \frac{1}{1 + \frac{E}{m_e c^2}(1 - \cos\theta)}\right] \quad (2)$$

where E is the incident photon energy, E' is the deposited energy of the scattered photon at location 204, $E_e$ is the recoiled electron 203 energy, θ is the angle between the flight direction of the scattered photon 205, the flight direction for the incident photon had it not collided 206, and location 202, $m_e$ is the mass of the recoiled electron 203, and c is the speed of light.

Assuming E' was measured by the layer stacked PET scanner 100, $E_e$ was measured by the layer stacked PET scanner 100, $m_e$=9.10938356×10$^{-31}$ kilograms, and c=299,792,458 meters per second, equation (1) and equation (2) can be used to solve for θ and E.

In other words, if the detector can record the recoiled electron 203 energy and location 202, which will be referred to herein as event 1 (i.e. Compton scatter event), and the scattered photon energy and location 204, which will be referred to herein as event 2 (i.e. second event) (where Compton scattering of the Compton scatter event causes the second event), the range of possible flight directions for the incident photon can be predicted.

A range of possible flight directions for the incident photon can be created using location 202, location 204, and θ. The range of possible flight directions can be defined as the possible regions where a true coincidence event could have occurred. In one embodiment, the range of possible flight directions can be defined by the walls of a cone shaped shell projection indicating flight directions the incident photon could potentially have taken, thereby enabling determining whether an event pair caused by an annihilation event is a true or scatter/random coincidence. For example, as illustrated in FIG. 2B, the range of possible flight directions creates a cone shaped shell projection 206 that has an apex point at location 202, an axis 207 that lines up with the flight direction of the scattered photon 205, and a half angle of θ. A GRD that lies on the wall of the cone shaped shell projection 206 can be considered to be within the range of possible flight directions. Notice that the actual flight direction for the incident photon 201 is within the cone shaped shell projection 206, and thus within the estimated range of possible flight directions.

The PET scanner 100 can use the above-mentioned techniques to determine whether a coincidence event is true or not. An example is shown using FIG. 3. An annihilation event 310 in OBJ causes a first incident photon to initially deposit in GRD1 and a second incident photon to initially head towards GRD22, but then scatter and deposit in GRD16. Thus, a (scattered/not true) coincidence event is detected between GRD1 and GRD16.

Event 1 302 and a Compton scattered event 2 304 are detected in L1 and L2 of GRD1, respectively. In GRD16, only a first event 309 is detected in L3 (no Compton scattering). The processor 107 can use the collected information of event 1 302 and event 2 304, along with the above mentioned techniques to estimate a range of possible flight directions, which is shown by the cone shaped shell projection 306. The possible flight directions are indicated by the walls (i.e. outer region) of the cone shaped shell projection 306 that overlap with a GRD. GRDs within the cone shaped shell projection 306 are not included as a possible flight direction. In this scenario, the range of possible flight directions includes GRD22 and GRD28. Therefore, because GRD16 is not within the range of possible flight directions (i.e. not one of the GRDs lying on the cone shaped shell projection 306), the coincidence event between GRD1 and GRD16 is not recorded as a true event. Notice that if the second incident photon had not scattered, it would have deposited in GRD22, which is in the range of possible flight directions, and thus would have been recorded as a true coincidence event.

Figure 3:
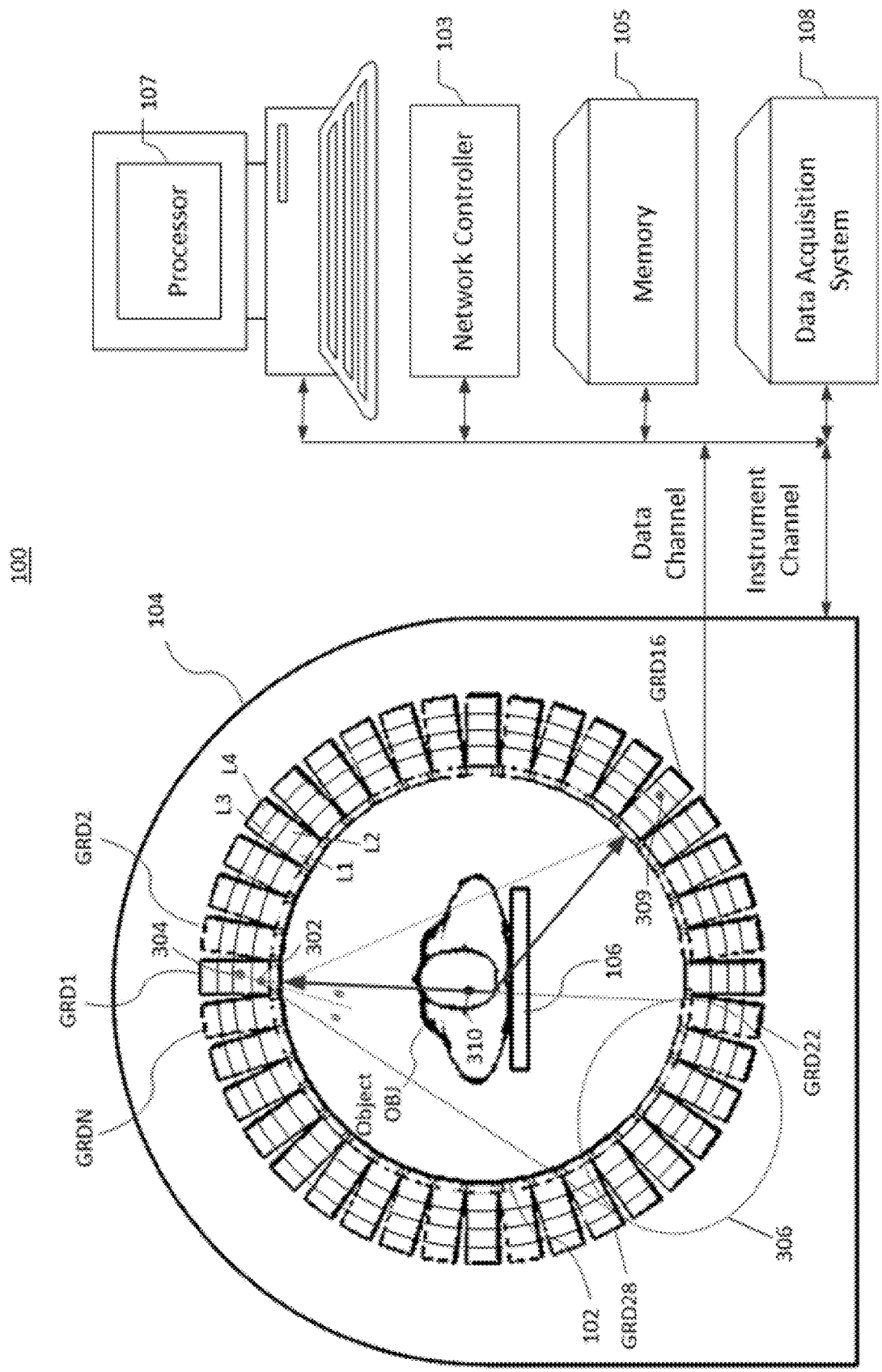
FIG. 3 illustrates an example of estimating a range of possible flight directions in the layer stacked PET scanner system of FIG. 1.

Note that the example in FIG. 3 had event 1 302 and event 2 304 occurring in the same GRD (GRD1), but in other embodiments, event 1 302 and event 2 304 can occur in different GRDs, so long as event 1 302 and event 2 304 are Compton scattered events of each other. For example, the above mentioned techniques can still work if event 1 302 occurs in L1 of GRD1, and event 2 304 occurs in L2 of GRD2.

Note that in some cases, event 2 can be followed by another Compton scattered event. Subsequent events can be used to confirm that the range of possible flight directions is correct. For example, event 2 and a subsequent Compton scattered event can use the above mentioned techniques to verify that the location of event 1 is accurate by creating a second cone shaped shell projection that should capture event 1.

Random and scattered coincidence events can be rejected using the above-mentioned techniques. Furthermore, the range of possible flight directions can be used as prior information in image reconstruction. A coincidence event that is not found to be true won't be included in the image, which can increase the image's overall quality.

Figure 4:
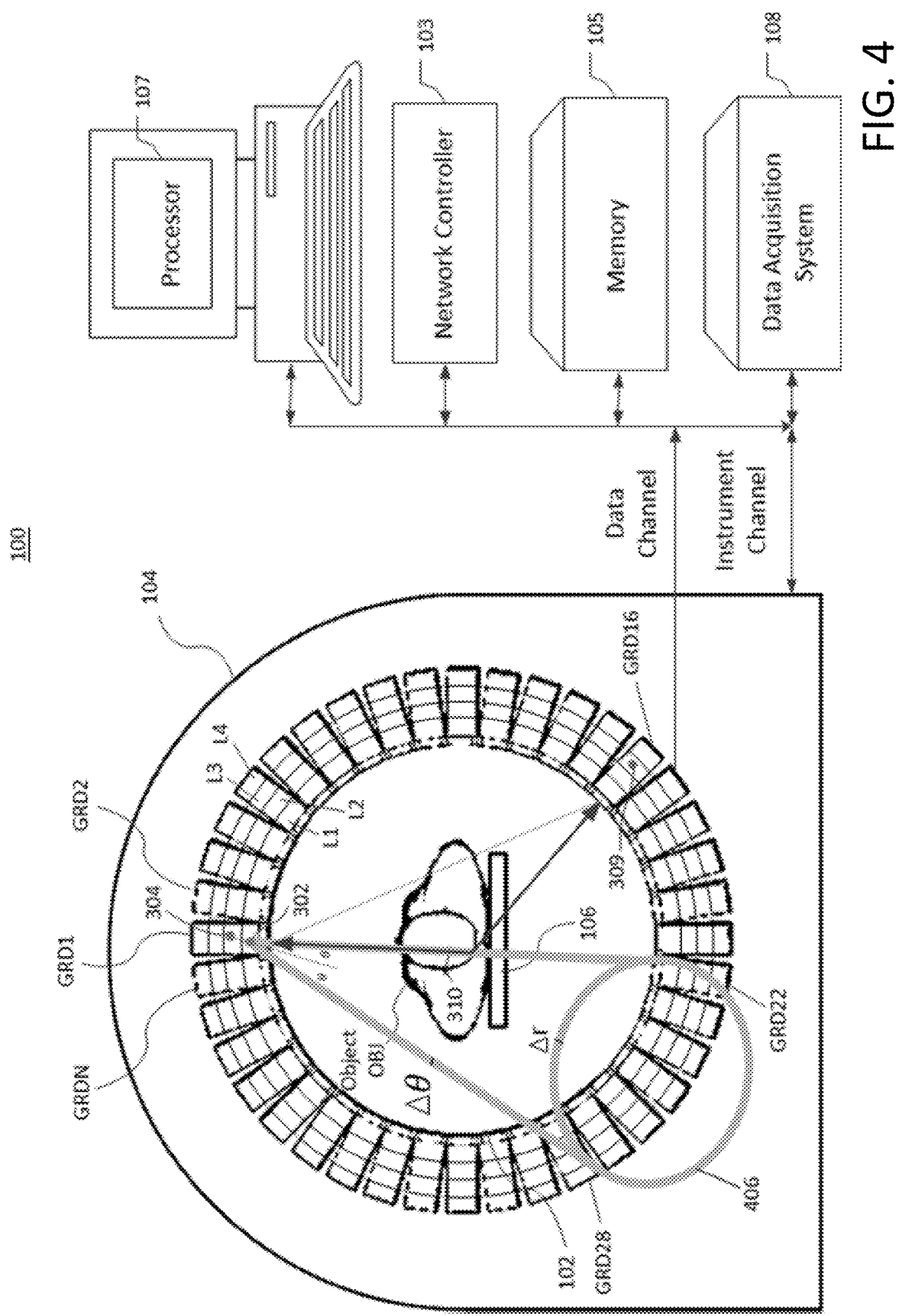
FIG. 4 illustrates an example of expanding the range of possible flight directions to account for a limited energy resolution and a limited spatial resolution in the layer stacked PET scanner system of FIG. 1.

To account for the layer stacked PET scanner's 100 limited energy resolution and/or limited spatial resolution, the range of possible flight directions can be expanded. In other words, the walls of the cone shaped shell projection 306 from FIG. 3 can become thicker. As shown in FIG. 4, the angle uncertainty Δθ and position uncertainty Δr increases the range of possible flight directions to create a thicker cone shaped shell projection 406. One or both of these uncertainty factors can be factored in by the processor 107 when determining the range of possible flight directions. In this scenario, the range of possible flight directions includes GRD22 and GRD28.

Expanding the range of possible flight directions by accounting for a variability of the energy caused by a limited energy resolution in the layer stacked PET scanner 100 can include identifying an angle uncertainty (AO). The angle uncertainty (AO) caused by limited energy resolution can be determined by equation (3) below:

$$\Delta\theta = \frac{(1 + \alpha(1 - \cos\theta))^2}{E \times \alpha \sin\theta} \Delta E_e \qquad (3)$$

where $E_e$ is the recoil electron energy, E is the incident gamma ray energy, and $\alpha = E/m_e c^2$. For a 511 keV gamma ray, $\alpha = 1$.

Expanding the range of possible flight directions by accounting for a variability of the location caused by a limited spatial resolution in the PET scanner 100 can include identifying a position uncertainty (dr). The position uncertainty (dr) caused by limited spatial resolution can be determined using equation (4) below:

$$\Delta r = \sqrt{\Delta x_1^2 + \Delta y_1^2 + \Delta z_1^2 + \Delta x_2^2 + \Delta y_2^2 + \Delta z_2^2} \qquad (4)$$

where $x_1$, $y_1$, and $z_1$ are the dimensions of the scintillator crystal where event 1 occurred, and $x_2$, $y_2$, and $z_2$ are the dimensions of the scintillator crystal where event 2 occurred.

As can be appreciated by one of ordinary skill in the art, the present disclosure can be embodied as a method. FIG. 5 is a flowchart of one method 500 according to an exemplary aspect of the present disclosure. Step 501 of method 500 is identifying a possible coincidence event between a first gamma ray detector for detecting first annihilation gamma rays and a second gamma ray detector for detecting second annihilation gamma rays. According to one exemplary aspect, the first and second gamma ray detectors are part of a layer stacked PET detector, comprise yttrium oxyorthosilicate, comprise silicon photomultipliers, or any combination thereof.

Step 503 of method 500 is estimating a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector. The range of possible flight directions for the first annihilation gamma ray detected in the first gamma ray detector can be based on a location of the Compton scatter event in the first gamma ray detector, an energy of the Compton scatter event in the first gamma ray detector, a location of a second event, and an energy of the second event, said second event caused by the Compton scatter event. As previously described, the range of possible flight directions can correspond to a cone shaped shell projection, according to one exemplary embodiment.

The range of possible flight directions can include flight directions based on a variability of the energy of the Compton scatter event and the energy of the second event, the variability being caused by a limited energy resolution of the nuclear medical diagnostic apparatus, as described previously.

The range of possible flight directions can include flight directions based on a variability of the location of the Compton scatter event and the location of the second event, the variability being caused by a limited spatial resolution of the nuclear medical diagnostic apparatus, as described previously.

Step 505 of method 500 determines whether the second gamma ray detector corresponds to the range of possible flight directions.

If the answer to step 505 is yes, step 507 is to assemble the possible coincidence event as a true coincidence event. If the answer to step 505 is no, step 509 is to not assemble the possible coincidence event as a true coincidence event.

The method and system described herein can be implemented in a number of technologies but generally relate to imaging devices and processing circuitry for performing the processes described herein. In one embodiment, the processing circuitry (e.g., image processing circuitry and controller circuitry) is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the calibration described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

Disclosed is a system and method aimed at directly determining the incident photon's direction(s) in a PET system. It is implemented by utilizing detected Compton events' energies and 3-D locations. In one embodiment, a layer stacked PET detector can be used for this implementation. The proposed method can constrain incident photon's direction to a cone shell. The thickness of the cone shell can be adjusted to account for the energy and location resolving accuracy of the PET detector. The disclosure provides a direct way to label each (or some) coincidence pair as true or scattered/random coincidence. A large portion of scatters within the prime energy window can be directly eliminated according to the incidental angles. Additionally, a large portion of random coincidences can be directly eliminated according to the event incident angles.

The incorporation of a layer stacked PET system offers numerous advantages. The layer stacked PET system discussed herein can be a LYSO/SiPM based layer stacked detector, which can ensure both in-general PET imaging quality and the additional benefit of scatter and random coincidence rejection. Furthermore, the system allows for broad configurations such as detecting events from a Compton scatter across multiple GRDs. Lastly, the incident photon's direction can be used as prior information to help with image reconstruction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Embodiments of the present disclosure may also be as set forth in the following parentheticals.

(1) A nuclear medical diagnostic apparatus comprising: first and second gamma ray detectors for detecting first and second annihilation gamma rays, respectively; processing circuitry configured to, identify a possible coincidence event between the first gamma ray detector and the second gamma ray detector; and estimate a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector (2) The apparatus of (1), wherein the processing circuitry is further configured to assemble the possible coincidence event as a true coincidence event if the second gamma ray detector corresponds to the range of possible flight directions and to not assemble the possible coincidence event as a true coincidence event if the second gamma ray detector does not correspond to the range of possible flight directions.

(3) The apparatus of any (1) to (2), wherein the processing circuitry configured to estimate the range of possible flight directions comprises processing circuitry configured to estimate the range of possible flight directions for the first annihilation gamma ray detected in the first gamma ray detector based on a location of the Compton scatter event in the first gamma ray detector, an energy of the Compton scatter event in the first gamma ray detector, a location of a second event, and an energy of the second event, wherein the second event is caused by the Compton scatter event.

(4) The apparatus of any (1) to (3), wherein the range of possible flight directions comprises flight directions based on a variability of the energy of the Compton scatter event and the energy of the second event, the variability being caused by a limited energy resolution of the nuclear medical diagnostic apparatus.

(5) The apparatus of any (1) to (4), wherein the range of possible flight directions comprises flight directions based on a variability of the location of the Compton scatter event and the location of the second event, the variability being caused by a limited spatial resolution of the nuclear medical diagnostic apparatus.

(6) The apparatus of any (1) to (5), wherein the range of possible flight directions corresponds to a cone shaped shell projection, the cone shaped shell projection having an apex point at the location of the Compton scatter event, an axis in line with the location of the Compton scatter event and the location of the second event, and a half angle based on the energy of the Compton scatter event and the energy of the second event.

(7) The apparatus of any (1) to (6), wherein the nuclear medical diagnostic apparatus is a layer stacked PET detector.

(8) The apparatus of any (1) to (7), wherein the first gamma ray detector and the second gamma ray detector comprise lutetium yttrium oxyorthosilicate.

(9) The apparatus of any (1) to (8), wherein the first gamma ray detector and the second gamma ray detector comprise one or more silicon photomultipliers.

(10) A method for collecting coincidence data in a nuclear medical diagnostic apparatus having a first and second gamma ray detector for detecting first and second annihilation gamma rays, respectively, comprising: identifying a possible coincidence event between the first gamma ray detector and the second gamma ray detector; and estimating a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector.

(11) The method of (10), further comprising: assembling the possible coincidence event as a true coincidence event if the second gamma ray detector corresponds to the range of possible flight directions and to not assemble the possible coincidence event as a true coincidence event if the second gamma ray detector does not correspond to the range of possible flight directions.

(12) The method of any (10) to (11), wherein the estimating the range of possible flight directions comprises estimating the range of possible flight directions for the first annihilation gamma ray detected in the first gamma ray detector based on a location of the Compton scatter event in the first gamma ray detector, an energy of the Compton scatter event in the first gamma ray detector, a location of a second event, and an energy of the second event, wherein the second event is caused by the Compton scatter event.

(13) The method of any (10) to (12), wherein the range of possible flight directions comprises flight directions based on a variability of the energy of the Compton scatter event and the energy of the second event, the variability being caused by a limited energy resolution of the nuclear medical diagnostic apparatus.

(14) The method of any (10) to (13), wherein the range of possible flight directions comprises flight directions based on a variability of the location of the Compton scatter event and the location of the second event, the variability being caused by a limited spatial resolution of the nuclear medical diagnostic apparatus.

(15) The method of any (10) to (14), wherein the range of possible flight directions corresponds to a cone shaped shell projection, the cone shaped shell projection having an apex point at the location of the Compton scatter event, an axis in line with the location of the Compton scatter event and the location of the second event, and a half angle based on the energy of the Compton scatter event and the energy of the second event.

(16) The method of any (10) to (15), wherein the nuclear medical diagnostic apparatus is a layer stacked PET detector.

(17) The method of any (10) to (16), wherein the first gamma ray detector and the second gamma ray detector comprise lutetium yttrium oxyorthosilicate.

(18) The method of any (10) to (17), wherein the first gamma ray detector and the second gamma ray detector comprise one or more silicon photomultipliers.

(19) A non-transitory computer-readable medium including computer-readable instructions that, when executed by a computing system, cause the computing system to sort data by performing a method comprising: identifying a possible coincidence event between a first gamma ray detector for detecting a first annihilation gamma ray and a second gamma ray detector for detecting a second annihilation gamma ray; and estimating a range of possible flight directions for the first annihilation gamma ray detected in the first gamma ray detector based on a Compton scatter event which is detected by the first gamma ray detector, wherein the possible coincidence event includes the Compton scatter event detected by the first gamma ray detector.

The invention claimed is:

1. A nuclear medical diagnostic apparatus, comprising:
    first and second gamma ray detectors for detecting first and second annihilation gamma rays, respectively;
    processing circuitry configured to
        identify a possible coincidence event between the first gamma ray detector and the second gamma ray detector;
        estimate a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector;
        determine whether the second gamma ray detector is located within the estimated range of possible flight directions; and
        count the possible coincidence event as a true coincidence event when determining that the second gamma ray detector is located within the range of possible flight directions, and not count the possible coincidence event as a true coincidence event when determining that the second gamma ray detector is not located within the range of possible flight directions.

2. The apparatus of claim 1, wherein the processing circuitry is further configured to estimate the range of possible flight directions for the first annihilation gamma ray detected by the first gamma ray detector based on a location of the Compton scatter event in the first gamma ray detector, an energy of the Compton scatter event in the first gamma ray detector, a location of a second event, and an energy of the second event, wherein the second event is caused by the Compton scatter event.

3. The apparatus of claim 2, wherein the range of possible flight directions estimated by the processing circuitry comprises flight directions based on a variability of the energy of the Compton scatter event and the energy of the second event, the variability being caused by a limited energy resolution of the nuclear medical diagnostic apparatus.

4. The apparatus of claim 2, wherein the range of possible flight directions estimated by the processing circuitry comprises flight directions based on a variability of the location of the Compton scatter event and the location of the second event, the variability being caused by a limited spatial resolution of the nuclear medical diagnostic apparatus.

5. The apparatus of claim 2, wherein the range of possible flight directions estimated by the processing circuitry corresponds to a cone-shaped shell projection, the cone-shaped shell projection having an apex point at the location of the Compton scatter event, an axis in line with the location of the Compton scatter event and the location of the second event, and a half angle based on the energy of the Compton scatter event and the energy of the second event.

6. The apparatus of claim 1, wherein the nuclear medical diagnostic apparatus is a layer stacked PET detector.

7. The apparatus of claim 1, wherein the first gamma ray detector and the second gamma ray detector comprise lutetium yttrium oxyorthosilicate.

8. The apparatus of claim 1, wherein the first gamma ray detector and the second gamma ray detector comprise one or more silicon photomultipliers.

9. A method for collecting coincidence data in a nuclear medical diagnostic apparatus having a first and second gamma ray detector for detecting first and second annihilation gamma rays, respectively, the method comprising:
identifying a possible coincidence event between the first gamma ray detector and the second gamma ray detector;
estimating a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector;
determining whether the second gamma ray detector is located within the estimated range of possible flight directions; and
counting the possible coincidence event as a true coincidence event when determining that the second gamma ray detector is located within the range of possible flight directions, and not counting the possible coincidence event as a true coincidence event when determining that the second gamma ray detector is not located within the range of possible flight directions.

10. The method of claim 9, wherein the estimating the range of possible flight directions comprises estimating the range of possible flight directions for the first annihilation gamma ray detected by the first gamma ray detector based on a location of the Compton scatter event in the first gamma ray detector, an energy of the Compton scatter event in the first gamma ray detector, a location of a second event, and an energy of the second event, wherein the second event is caused by the Compton scatter event.

11. The method of claim 10, wherein the range of possible flight directions estimated in the estimating step comprises flight directions based on a variability of the energy of the Compton scatter event and the energy of the second event, the variability being caused by a limited energy resolution of the nuclear medical diagnostic apparatus.

12. The method of claim 10, wherein the range of possible flight directions estimated in the estimating step comprises flight directions based on a variability of the location of the Compton scatter event and the location of the second event, the variability being caused by a limited spatial resolution of the nuclear medical diagnostic apparatus.

13. The method of claim 10, wherein the range of possible flight directions estimated in the estimating step corresponds to a cone-shaped shell projection, the cone-shaped shell projection having an apex point at the location of the Compton scatter event, an axis in line with the location of the Compton scatter event and the location of the second event, and a half angle based on the energy of the Compton scatter event and the energy of the second event.

14. The method of claim 9, wherein the nuclear medical diagnostic apparatus is a layer stacked PET detector.

15. The method of claim 9, wherein the first gamma ray detector and the second gamma ray detector comprise lutetium yttrium oxyorthosilicate.

16. The method of claim 9, wherein the first gamma ray detector and the second gamma ray detector comprise one or more silicon photomultipliers.

17. A non-transitory computer-readable medium including computer-readable instructions that, when executed by a computing system, cause the computing system to perform a method comprising:
identifying a possible coincidence event between a first gamma ray detector for detecting a first annihilation gamma ray and a second gamma ray detector for detecting a second annihilation gamma ray;
estimating a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector;
determining whether the second gamma ray detector is located within the estimated range of possible flight directions; and
counting the possible coincidence event as a true coincidence event when determining that the second gamma ray detector is located within the range of possible flight directions, and not counting the possible coincidence event as a true coincidence event when determining that the second gamma ray detector is not located within the range of possible flight directions.

18. A nuclear medical diagnostic apparatus, comprising:
first and second gamma ray detectors for detecting first and second annihilation gamma rays, respectively;
processing circuitry configured to
identify a possible coincidence event between the first gamma ray detector and the second gamma ray detector;
estimate a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector; and
count the possible coincidence event as a true coincidence event when the second gamma ray detector is located within the range of possible flight directions, and not count the possible coincidence event as a true coincidence event when the second gamma ray detector is not located within the range of possible flight directions,
wherein the processing circuitry is further configured to:
determine a first range of possible flight directions for the first annihilation gamma ray based on a location of the Compton scatter event detected by the first gamma ray detector and an energy of the Compton scatter event detected by the first gamma ray detector, and
expand the determined first range so as to determine, as the estimated range, a second range larger than the first range, the second range being determined based on a spatial resolution of the detected location and an energy resolution of the detected energy.

19. A method for collecting coincidence data in a nuclear medical diagnostic apparatus having a first and second gamma ray detector for detecting first and second annihilation gamma rays, respectively, the method comprising:
identifying a possible coincidence event between the first gamma ray detector and the second gamma ray detector;
estimating a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector; and counting the possible coincidence event as a true coincidence event when the second gamma ray detector is located within the range of possible flight directions, and not counting the possible coincidence event as a true coincidence event when the second gamma ray detector is not located within the range of possible flight directions, wherein the method further comprises:

determining a first range of possible flight directions for the first annihilation gamma ray based on a location of the Compton scatter event detected by the first gamma ray detector and an energy of the Compton scatter event detected by the first gamma ray detector, and expanding the determined first range so as to determine, as the estimated range, a second range larger than the first range, the second range being determined based on a spatial resolution of the detected location and an energy resolution of the detected energy.

20. A non-transitory computer-readable medium including computer-readable instructions that, when executed by a computing system, cause the computing system to perform a method comprising:

identifying a possible coincidence event between a first gamma ray detector for detecting a first annihilation gamma ray and a second gamma ray detector for detecting a second annihilation gamma ray;

estimating a range of possible flight directions for the first annihilation gamma ray detected by the first gamma ray detector based on a Compton scatter event, which is detected by the first gamma ray detector, wherein the possible coincidence event includes the Compton scatter event detected by the first gamma ray detector; and counting the possible coincidence event as a true coincidence event when the second gamma ray detector is located within the range of possible flight directions, and not counting the possible coincidence event as a true coincidence event when the second gamma ray detector is not located within the range of possible flight directions, wherein the method further comprises:

determining a first range of possible flight directions for the first annihilation gamma ray based on a location of the Compton scatter event detected by the first gamma ray detector and an energy of the Compton scatter event detected by the first gamma ray detector, and expanding the determined first range so as to determine, as the estimated range, a second range larger than the first range, the second range being determined based on a spatial resolution of the detected location and an energy resolution of the detected energy.

* * * * *